(12) United States Patent
Matta et al.

(10) Patent No.: US 8,163,473 B2
(45) Date of Patent: Apr. 24, 2012

(54) METHOD FOR USING DNA REPAIR CAPACITY AS A BIOMARKER OF BREAST CANCER RISK IN WOMEN

(75) Inventors: Jaime Matta, Ponce, PR (US); Manuel Bayona, Ponce, PR (US)

(73) Assignees: Jaime L. Matta Murias, Ponce, PR (US); Manuel Bayona Cells, Ponce, PR (US)

( * ) Notice: Subject to any disclaimer, the term of this patent is extended or adjusted under 35 U.S.C. 154(b) by 199 days.

(21) Appl. No.: 12/453,250

(22) Filed: May 5, 2009

(65) Prior Publication Data

US 2010/0285456 A1    Nov. 11, 2010

(51) Int. Cl.
*C12Q 1/00* (2006.01)
(52) U.S. Cl. ......................................................... 435/4
(58) Field of Classification Search ........................ None
See application file for complete search history.

(56) References Cited

OTHER PUBLICATIONS

Ramos et al (Cancer, 2004, 100(7): 1352-1357).*

* cited by examiner

*Primary Examiner* — Sean Aeder

(57) ABSTRACT

The present invention presents a method for using DNA repair capacity (DRC) as a blood biomarker to calculate the risk of a female subject developing breast cancer obtained from a blood sample by using a luciferase reporter gene method that permits calculating a percent DRC for the subject. A subject with a percent DRC below 3.1% is considered as being at risk for breast cancer and a subject with a percent DRC above 3.1% as being at low risk for breast cancer. This method comprises a further estimation of an adjusted risk of the subject to develop breast cancer using a logistic regression equation in which the DRC value is included as one of the variables.

2 Claims, 2 Drawing Sheets

METHOD FOR USING DNA REPAIR CAPACITY AS A BIOMARKER OF BREAST CANCER RISK IN WOMEN

CROSS-REFERENCE TO RELATED APPLICATIONS

Domestic Priority patent Ser. No. 12/453,250; Title: Method for using DNA repair capacity as a biomarker of breast cancer risk in women; Inventors: Matta, Jaime, Bayona Manuel

REFERENCES CITED

Athas, W F, Hedayati M A, Matanoski G M, Farmer E R, and L Grossman. 1991. Development and field-test validation of an assay for DNA repair in circulating human lymphocytes. Cancer Res. 21:5786-5796.

Beenken S W, Grizzle W E, Crowe D R, Conner M G, Weiss H L, Sellers M T, Krontiras H, Urist M M and K I Bland. 2001. Molecular biomarkers for breast cancer prognosis: coexpression of c-erbB-2 and p53. Ann Surg. 233:630-638.

Bishop, J M. 1995. Cancer: The rise of the genetic paradigm, Genes & Dev., 9, 1309-1315.

Cheng L, Eicher S A, Guo Z, Hong W K, Spitz M R, and Q Wei. 1998. Reduced DNA repair capacity in head and neck cancer patients. Cancer Epidemiol. Biomarkers Prev. 7:465-468.

Coleman M, Shen M R, Peterson G, Jones I, and H W Mohrenweiser. 1998. DNA repair gene variants as cancer susceptibility factors. Proc. Amer. Assoc. Cancer Res. 39.

Culotta, E and D E Koshland Jr 1993. p53 sweeps through cancer research. Science. 262:1958-1961.

Echols H and M F Goodman. 1991. Fidelity mechanisms in DNA replication, Annu. Rev. Biochem. 60: 477-511.

Gordis, L. 2008. Epidemiology, 4$^{th}$ edition, W.B. Saunders Co.

Griner P F, Mayewski R J, Mushlin A I and P Greenland. 1981. Selection and interpretation of diagnostic tests and procedures. Annals of Internal Medicine, 94: 555-600.

Grossman L and Q Wei. 1994. DNA repair capacity (DRC) as a biomarker of human variational responses to the environment. In: DNA Repair Mechanisms: Impact on Human Diseases and Cancer, H. Vos, J. M. (ed.) R. G. Landes Company. pp. 329-347.

Hayes D F, Bast R C, Desch C E, Fritsche H Jr, Kemeny N E, Jessup J M, Locker G Y, Macdonald J S, Mennel R G, Norton L, Ravdin P, Taube S and R J Winn. 1996. Tumor marker utility grading system: A framework to evaluate clinical utility of tumor markers. J Natl Cancer Inst. 88:1456-1466.

Helzlsouer K J, Harris E L, Parshad R, Perry H R, Proce F M and K K Sanford. 1996. DNA repair proficiency: Potential susceptibility factor for breast cancer, J. Natl. Cancer. Inst. 88: 754-755.

Helleday, T, Petermann E, Lundin C, Hodgson B and R A Sharma. 2008. DNA repair pathways as targets for cancer therapy. Nat. Rev. Cancer. 8:193-204.

Hinestrosa M C, Dickersin K, Klein P, Mayer M, Noss K, Slamon D, Sledge G and F M Visco. 2007 Opinion: Shaping the future of biomarker research in breast cancer to ensure clinical relevance. Nature Reviews Cancer 7: 309-315.

Hosmer D W, and S 2004 Applied Logistic Regression, 2nd Edition. Wiley Series in Probability and Statistics. John Wiley and Sons, New Jersey.

Hu, Z, Wang, L E and Q Wei. 2007. Molecular epidemiology of DNA repair and cancer susceptibility-A review of population-based studies. In: DNA Repair, Genetic Instability and Cancer (Wei et al. eds.), World Scientific, pp. 315-344.

Hu, J J. 2004. Genetic variations in DNA repair: Their implications in human cancer risk, prevention and therapy, In: DNA Repair in Cancer Therapy, Panasci, L. C., Alaoui-Jamali, M. A. (eds.), Humana Press, pp. 339-351.

Jyothish B R, Ankathi B, Chandini B, Vinodkumar G, Nayar S, Roy D, Madhavan J and M K Nair. 1998. DNA repair proficiency: a potential marker for identification of high risk members in breast cancer families, Cancer Lett. 124: 9-13.

Landi M T, Baccarelli A, Tarone R E et al. 2002. DNA repair, dysplastic nevi, and sunlight sensitivity in the development of cutaneous malignant melanoma. J. Natl. Cancer Inst. 94:94-101.

Livneh Z, Cohen-Fix O, Skaliter R and T Elizur. 1993. Replication of damaged DNA and the of ultraviolet light mutagenesis, CRC Crit. Rev. Biochem. Mol. Biol., 28, 465-513.

Matta J L, Villa J L, Ramos J M, Sanchez J, Chompre, G, Ruiz A and L Grossman. 2003. DNA repair and non-melanoma skin cancer in Puerto Rican populations. J. Am. Acad. Dermatol. 49:433-439.

Metz C E. 1978. Basic principles of ROC analysis. Seminars in Nuclear Medicine. 8: 283-298.

Mohrenweiser H and I Jones. 1998. Variation in DNA repair is a factor in cancer susceptibility: a paradigm for the promises and perils of individual and population risk estimation. Mutat. Res. 400:15-24.

Murray D and A C Berg. 2004. Relationship among DNA repair genes, cellular radiosensitivity, and the response of tumors and normal tissues to radiotherapy. In: DNA Repair in Cancer Therapy, Panasci, L. C., Alaoui-Jamali, M. A. (eds.), Humana Press, pp. 211-256.

Patel, R K, Trivedi, A H, Arora, D C, Bhatavdekar, J M and D D Patel. 1997. Int. J. Cancer. 73:20-24.

Qiao, Y, Spitz, M R., Guo, Z, Hadeyati, M, Grossman, L, Kraemer, K H and Q Wei. 2002. Rapid assessment of repair of ultraviolet DNA damage with a modified host-cell reactivation assay using a luciferase reporter gene and correlation with polymorphisms of DNA repair genes in normal human lymphocytes. Mut. Res. 509:165-174.

Ramos J. M., Ruiz A., Colen R., Lopez I. D., Grossman L. and J. L. Matta. 2004. DNA repair and breast cancer susceptibility in women. Cancer 100:1352-1357.

Shi Q, Wang L E, Bondy M L, Brewster A, Singletary S E and Q Wei. 2004. Reduced DNA repair of benzo(a) pyren diol epoxide-induced adducts and common XPD polymorphisms in breast cancer patients. Carcinogenesis, April 16, epub.)

Vogelstein B and K W Kinzler. 1993. The multistep nature of cancer. Trends Genet. 9: 138-141.

Wei Q, Matanoski G M, Farmer E R, Hedayati M A and L Grossman. 1993. DNA repair and aging in basal cell carcinoma: a molecular epidemiology study. Proc. Natl. Acad. Sci. USA 90:1614-1618.

Wei Q, Matanoski G M, Farmer E R, Hedayati M A and L Grossman. 1994. DNA repair and susceptibility to basal cell carcinoma: a case-control study, Am. J. Epidemiol., 140:598-607.

Wei Q L, Cheng W K, Hong and M R Spitz. 1996. Reduced DNA repair capacity in lung cancer patients, Cancer Res. 56: 4103-4107.

Wei Q, Lee J E, Gershenwald, J E et al. 2003. Repair of UV light induced DNA damage and risk of cutaneous malignant melanoma. J. Nat. Cancer Inst. 95:308-314.

Weinberg, R A. 2007. The Biology of Cancer. Garland Science, Taylor & Francis Group, 796 pp.

Winchester, D J, Winchester, D P, Hudis, C A and L Norton (eds.). 2006. Breast Cancer, Second Edition, BC Decker Inc., 607 pp.

Wood, W C, Muss, H B, Solin, L J and O I Olopade. 2005. Malignant tumors of the breast. In: Cancer: Principles & Practice of Oncology, pp. 1415-1477, 7$^{th}$ edition, DeVita, V. T., Hellman, S, Rosenberg, S. A. (eds.), Lippincott-Raven Publishers.

World Health Organization (WHO). 2000. Cancer incidence, mortality, and prevalence worldwide. Globocan 2000. Available from URL: www.dep.iarc.fr/globocan/globocan.html.

Zweig M H and G Campbell. 1993. Receiver-operating characteristic (ROC) plots: a fundamental evaluation tool in clinical medicine. Clinical Chemistry. 39: 561-577.

FOREIGN PATENT DOCUMENTS n/a

OTHER PUBLICATIONS n/a

FIELD OF THE INVENTION

The present invention relates to the fields of differential diagnosis, risk assessment and screening of breast cancer in women. The present invention is focused on the development of a breast cancer biomarker; more specifically a method for determining a risk of a woman to develop and/or be free from breast cancer based on associations of its overall DNA repair capacity as determined in blood lymphocytes with breast cancer.

DESCRIPTION OF RELATED ART

Breast carcinoma (BC) is the most common cancer worldwide affecting woman, accounting for 20% of all malignancies in women (Globocan 2000). The estimated annual incidence of BC worldwide is about one million cases (Dumitrescu and Cotarla 2005). It is estimated that over 3 million women are living with breast carcinoma in the United States (NCI-SEER 2004). Approximately 216,000 women were diagnosed with invasive BC in the year 2004 and 40,110 died of this disease in the USA (Wood et al. 2005, SEER 2004). It is also estimated that there will be 62,000 new cases of in situ (non-invasive) breast cancer. The growing incidence of breast cancer underscores our gap in knowledge about what causes this disease and the lack of acceptable preventive interventions. Fewer than 10% of women who develop breast cancer have an identifiable inherited susceptibility to the disease, while another 15%-20% have a family history but no readily identifiable genetic pattern.

Despite the declining trend in mortality, breast cancer is currently the second leading cause of cancer deaths in U.S. women and will kill about 40,970 women and 460 men in 2006. Included among these deaths are women diagnosed with "early" breast cancer, who received the full-blown complement of surgical and adjuvant treatment and who anticipated being among the 98% who would be alive at 5 years. Current clinical guidelines recommend that one or more modalities of treatment be provided for nearly all invasive and noninvasive breast cancers. Included among these treatments are painful and disfiguring surgeries and toxic therapies that result in severe side effects. Despite these treatments, no one with breast cancer can ever be sure that she or he is cured of the disease (WHO, 2000). The reported 5-year survival rate for localized breast cancer (i.e. invasive disease that has not spread to the lymph nodes or elsewhere outside the breast) is 98% but drops to 81% for those whose cancer has spread regionally and to 26% for those with distant metastases. The 10-year survival rate for all women in the United States diagnosed with invasive breast cancer is only 80% (WHO, 2000).

Defining molecular abnormalities in breast cancer is an important strategy for early detection, assessment of prognosis, and treatment selection (Beenken et al. 2001). In recent years, government, academia, industry, and foundations have devoted vast resources to identifying and developing biomarkers that can help determine which treatments afford the greatest benefit to a given individual with breast cancer. A biomarker is defined as any cellular, sub-cellular or humoral factor that demonstrates the presence of malignancy or malignant potential, or predicts tumor behavior, prognosis or response to treatment. The earlier we are able to detect breast cancer, the better the outcome (prognosis). In addition to improving survival through selecting the best treatments for an individual, the use of breast cancer biomarkers can improve patients' quality of life by sparing them from toxic treatments that are not likely to be of personal benefit. Biomarkers also have the potential to identify individuals at high risk for breast cancer who might benefit from preventive interventions. Hayes et al. 1996 have identified at least six ways in which cancer biomarkers may be used. These are:

1. Risk assessment. Classify women into risk categories which can be helpful for determining how often a woman should be screened and whether any preventive measures would be appropriate.

2. Screening. Screen large numbers of healthy women and women at high risk to detect breast cancer at its earliest stages.

3. Differential diagnosis. Use in conjunction with other clinical parameters, such as biopsy and radiological findings in high risk groups, to determine that disease is present.

4. Prognosis. Potential to predict relapse or progression independent of future treatment effects.

5. Prediction. Potential to predict response or resistance to a specific therapy.

6. Monitor course. Potential to detect relapse in patient with no evidence of disease after therapy for primary or recurrent disease, or follow detectable disease in patient to determine whether the current therapeutic regimen is effective.

Two biomarkers have proven clinically significantly useful in breast cancer, demonstrating both prognostic and predictive properties among women who already developed the disease: ER and HER2/neu. These two estrogen receptor biomarkers have had major impacts on the way in which breast cancer is treated. Interventions targeted to these biomarkers have decreased relapse rates in women with these specific tumor characteristics. Very little has changed in the last few years; ER and HER2/neu remain the only biomarkers meriting widespread clinical use. Researchers now recognize the need to develop and validate standardized assays with consistent scoring systems, differentiate between prognostic effects and predictive effects, and carefully select appropriate clinical endpoints.

The capacity to maintain genome integrity is critical for preventing genetic alterations associated with the multistage progression of cancer (Cullotta and Koshland 1993). DNA repair functions as a major defense against environmental damage to cells in all organisms. Efficient DNA repair is critical in processes that minimize cell death, mutations, replication errors, and genomic instability (Hu 2004). DNA repair is a critical defense system in the human body aimed at protecting the integrity and stability of the genome. At least 230 DNA repair genes have been identified in the human body (www.cgal.icnet.uk). DNA repair genes play a critical role in protecting the genome from the harmful effects of cancer-causing agents (Murray and Berg 2004). When unrepaired DNA lesions are replicated, they cause mutations because of their miscoding nature (Echols and Goodman 1991, Livneh et al., 1993). The occurrence of such mutations in critical genes, e.g., oncogenes and tumor suppressor genes, may lead to the development of cancer (Bishop, 1995, Vogelstein and Kinzler, 1993, Weinberg, 2007). Indeed, DNA repair has emerged in recent years as a critical factor in cancer pathogenesis as a growing number of cancer predisposition syndromes have been shown to be caused by mutations in genes involved in DNA repair and the regulation of genome stability.

Human populations normally show a range of inherent sensitivities to mutagens and carcinogens. This can be partly explained by differences between individuals in their capacity to repair DNA damage as demonstrated by Grossman and Wei (1994). FIG. 1 show a comparison between women with and without breast cancer found in our breast cancer research.

Several highly conserved DNA repair pathways have evolved to repair DNA modifications caused by replication errors or DNA damage. Activation of oncogenes or deactivation of tumor suppressor genes due to specific mutations can have profound effects on the progression of many types of cancer. The linkage between persistent DNA damage and oncogene activity suggests that such long-lived DNA damage is a reflection of the diminished involvement of DNA maintenance and repair in tumorigenesis (Grossman and Wei 1994).

Several studies have conclude that individual variability in the DNA repair capacity of humans is correlated with variation in cancer susceptibility, with low repair correlated to higher cancer risk (Athas et al. 1991, Helzlsouer et al. 1996, Jyothish et al. 1998, Matta et al. 2003, Patel et al, 1997, Ramos et al. 2004, Wei et al., 1993, 1994, 1996). Currently, the most rapidly growing research areas are focusing on the association between DNA repair genotype and phenotype in human cancer susceptibility and response to cancer therapy (Hu 2004). Epidemiological studies among the broader population using functional repair assays in lymphocytes or other accessible cell types have also demonstrated that DNA repair capacity is highly variable among individuals and that a low repair capacity is a significant risk factor for the development of several types of cancers (Mohrenweiser and Jones 1998, Murray and Berg 2004). Associations between decreased repair activity and increased cancer risk among the general population initially became apparent from studies using assays that measure phenotypic repair in lymphocytes of DNA damage induced by some external agent, the use of plasmid or viral reactivation assays, or the measurement of levels and splicing patterns of repair-gene mRNAs and repair proteins themselves (Murray and Berg 2004).

Grossman and Wei (1994) have provided significant evidence for the usefulness of lymphocytes as surrogate cells for estimating DNA repair in epidemiological studies of skin cancer susceptibility. This observation has been extended to breast cancer in a study conducted by one of the inventors (Matta et al. 2004). This evidence is as follows: 1) Lymphocytes are the most amenable nucleated cells for population studies because of the minimal invasiveness required for sampling, 2) They are in equilibrium with virtually all cells in the body, 3) They are able to pass through the blood-brain barrier, 4) The DNA repair curve of lymphocytes is the same as the one published for established fibroblasts, lymphoblasts, and patients with DNA repair deficiencies, 5) In the landmark studies of the Nordic Study Group, it was found that chromosomal aberrations in lymphocytes invariably reflect cancer of the GI tract, lung, breast, female genital organs, prostate, urinary system, skin, brain lymphoma and leukemia, 6) The effect of age of the donor on DRC is the same for both, lymphocytes as well as for skin fibroblasts which are corrected for passage number, 7) One of the unexpected findings was the age-related decline in DRC, this underscores the values of lymphocytes because the mutation frequency for the hypoxanthine-guanine phosphoribosyl transferase (hprt) locus increases 1.3-1.6% per year, this reflects the same order of magnitude decline of DRC as a function of age; and, 8) Because of the genetic character of most DNA repair deficiency diseases, DRC levels should be reduced in most cells of these patients.

Many individuals have now been found to exhibit a decreased repair phenotype (typically 60-75% of normal) that is associated with an increased cancer risk from various environmental carcinogens (Murray and Berg 2004). For example, persons with a reduced capacity to repair DNA damage have increased susceptibility to non-melanoma and melanoma skin carcinoma (Wei et al. 1993, 2003, Matta et al. 2003), prostrate carcinoma (Hu et al. 2004), lung carcinoma (Wei et al. 1996), head and neck carcinomas (Cheng et al. 1998, Coleman et al. 1998). The pilot study conducted by Ramos et al. 2004 in which Jaime Matta (one of the inventors of this application) was the senior and correspondent author showed a significant average reduction of 36% in the age-adjusted DRC in women (n=40) with breast cancer when compared with age-adjusted controls (n=58) without this disease. Consumption of antioxidants is associated with an increased DNA repair capacity in lymphocytes (Matta et al. 2003). The association between breast cancer and polymorphisms in DNA repair enzymes was also supported by the study of Shi et al. 1994. This overall hypothesis was tested by means of a clinical, retrospective case-control study.

DNA repair has also recently received the attention of the scientists as a potential therapeutic target. For example, Helleday et al. 2008 have recently suggested that DNA repair pathways can enable cancer tumor cells to survive DNA damage that is induced by chemotherapeutic treatments. They proposed that inhibitors of specific DNA repair pathways might prove efficacious when used in combination with DNA-damaging chemotherapeutic drugs. In addition, alterations in DNA repair pathways that arise during tumor development can make some cancer cells reliant on a reduced set of DNA repair pathways for survival. Drugs that inhibit one of these pathways in such tumors could prove useful as single-agent therapies, with the potential advantage that this approach could be selective for tumor cells and have fewer side effects.

U.S. Pat. No. 6,358,682 by Jaffee et al. teaches a method, kit and controls for detecting HER-2/neu gene amplification as a predictor of breast cancer reoccurrence and patient survival. The method is a fluorescent in-situ hybridization (FISH) assay using a labeled DNA probe. By determining the genetic nature of the cancer cells, appropriate treatment may be utilized. Control tumor cell lines with predefined amounts of HER-2/neu gene amplification were also disclosed.

U.S. Pat. No. 7,097,977 by Takeda et al. teaches a method to provide a mutant Rad51 paralog gene, wherein a protein encoded thereby shows an activity for enhancing sensitivity of a cell to a DNA-damaging factor; a mutant Rad51 paralog peptide showing the activity; a transformed cell having the gene; a screening method for a drug having a DNA-damaging action, comprising contacting a test substance with the transformed cell, and evaluating a response of the cell; and a screening method for a controlling agent for DNA repair, comprising contacting a test substance with a transformed cell having the Rad51 paralog gene, and evaluating a homologous recombination repair capacity. According to the said invention, they enabled a screening of a novel anticancer agent which allows a more efficient therapy for cancer, wherein the agent is capable of enhancing the sensitivity of a cell to an anticancer agent comprising a DNA-damaging factor or an agent having a DNA-damaging action.

U.S. Pat. No. 7,354,713 by Mertz et al. teaches a method of using estrogen-related receptor gamma (ERR gamma) status to determine prognosis and treatment strategy for breast cancer, method of using ERR gamma as a therapeutic target for treating breast cancer, method of using ERR gamma to diagnose breast cancer, and method of using ERR.gamma. to identify individuals predisposed to breast cancer.

U.S. Pat. No. 0,003,454 by Livneh et al. teaches methods and kits for determining a risk to develop cancer, for evaluating an effectiveness and dosage of cancer therapy and for correlating between an activity of a DNA repair enzyme and a cancer.

U.S. Pat. No. 0,096,863 by Livneh et al. teaches methods and kits for determining a risk to develop cancer, for evaluating an effectiveness and dosage of cancer therapy and for correlating between an activity of a DNA repair enzyme and a cancer.

U.S. Pat. No. 7,319,007 by Cybulski et al. teaches a method and kits for determining a predisposition for developing cancer, e.g., prostate and/or breast cancer, due to a germline mutation of a NBS1 gene. The present invention also relates to surveillance protocols for developing cancer, e.g., prostate and/or breast cancer, due to germline mutation of a NBS1 gene.

U.S. Pat. No. 7,319,007 by Streckfus et al. teaches a method of diagnosing and monitoring malignant breast carcinomas using a panel of biomarkers in the saliva of a cohort of 1) healthy women, 2) women with benign lesions of the breast and 3) women with diagnosed breast cancer. Recognized tumor markers c-erbB-2 (erb), cancer antigen 15-3 (CA 15-3), and tumor suppresser oncogene protein 53 (p53) were found in the saliva of all three groups of women. The levels of erb and CA 15-3 in the cancer patients evaluated, however, were significantly higher than the salivary levels of healthy controls and benign tumor patients. Conversely, pantropic p53 levels were higher in controls as compared to those women with breast cancer and those with benign tumors.

U.S. Pat. No. 6,855,554 by Fritsche et al. teaches methods and compositions for detection of breast cancer. Systematic comparisons of breast ductal fluid samples obtained by nipple aspiration from women with unilateral breast cancer revealed significant differences in ductal fluid protein expression between the breast with cancer and the breast without cancer in each patient. This invention teaches that breast ductal fluid contains over 1000 separate protein species and that ductal fluids from breast cancer patients may be useful for high-throughput biomarker discovery.

U.S. Pat. No. 6,500,633 by Compton et al. teaches a method of detecting carcinomas by measuring the level of a glycerol compound, such as glycerol-3-phosphate, in a plasma, serum, or urine specimen from a patient. The method is thought to be particularly useful as a screening test for ovarian and breast carcinomas.

U.S. Pat. No. 6,282,305 by Huo et al. teaches a method and system for the computerized assessment of breast cancer risk using a digital image of a breast. This image of a breast is obtained and at least one feature and typically plural features are extracted from a region of interest in the digital image. The extracted features are compared with a predetermined model associating patterns of the extracted features with a risk estimate derived from corresponding feature patterns associated with a predetermined model based on gene carrier information or clinical information, or both gene carrier information and clinical information, and a risk classification index is output as a result of the comparison. Preferred features to be extracted from the digital image include 1) one or more features based on absolute values of gray levels of pixels in said region of interest, 2) one or more features based on gray-level histogram analysis of pixels in said region of interest; 3) one or more features based on Fourier analysis of pixel values in said region of interest; and 4) one or more features based on a spatial relationship among gray levels of pixels within the region of interest.

U.S. Pat. No. 6,218,529 by An et al. teaches the use of biomarkers and targets for diagnosis, prognosis and management of prostate, breast and bladder cancer. This invention discloses diagnostic techniques for the detection of human prostate, bladder and breast cancer. Genetic probes and methods useful in monitoring the progression and diagnosis of prostate, bladder and breast cancer are described. The invention relates particularly to probes and methods for evaluating the presence of RNA species that are differentially expressed in prostate, bladder and breast cancer compared to normal human prostate, benign prostatic hyperplasia, or normal bladder or breast tissue.

SUMMARY OF THE INVENTION

The present invention relates to a novel method of using the DNA repair capacity (DRC) of blood lymphocytes isolated from women to rule out the presence of breast cancer and/or use in differential diagnosis along with other diagnostic procedures to increase the probability of detecting or diagnosing it, ruling-it-out, and to identify women pre-disposed to it, in terms of differential diagnosis, screening, and breast cancer risk assessment respectively. This method could be a very valuable addition to various other screening, diagnostic and risk assessment tests for breast cancer. Examples on applicability of this method to a human population are presented. While there is no intention to displace any of them, the addition of said invention will increase current tests predictive values for breast cancer, and possibly other cancers in the future.

The current invention utilizes a well-established biostatistical and epidemiological method of determining the lifetime risk of developing breast cancer, using logistic regression modeling to estimate the probability to eventually develop breast cancer of a subject (Hosmer and Lemeshow, 2004) and uses a modification of the method first published by Athas et al. 1991 and subsequently modified by Qiao et al. 2002 to measure directly the level of DNA repair capacity (DRC) in lymphocytes (white blood cells) of women.

DRC of peripheral lymphocytes of patients with cancer and cancer-free controls are measured by means of a reactivation (HCR) assay with luciferase reporter gene used to measure DNA repair capacity in human lymphocytes. This assay comprises the following steps:

A plasmid carrying a luciferase reporter gene is damaged by UV light doses;

Extraction of peripheral lymphocites (PL) from human blood is performed. Media containing phytohemaglutinin P (PHAP) is added to PL and internal control cells for proliferation and incubated for 72 hours;

The treated plasmids are transfected using DEAE-Dextran method into the internal control cells and PL are given 40 hrs to repair the damaged reporter gene;

DRC is measured by the percent of reactivated luciferase activity relative to the untreated plasmid control (adapted from Grossman and Wei 1994);

Data is used later for DNA Repair Capacity determination of each person and subsequent statistical analysis.

This assay, which is not claimed in the present invention, provides a direct, global estimate of DNA repair without distinguishing between specific DNA repair pathways. It has the advantage that it provides a direct measurement of DRC in contrast with other assays that measure DRC indirectly (e.g. unscheduled DNA synthesis). A luciferase reporter gene is used because this plasmid construct is more sensitive, faster, and less expensive and does not require the use of radioactivity (Qiao et al. 2002).

Using clinical and epidemiological data generated by the inventors in a large scale population study of over 725 women with and without breast cancer (case-control study), the inventors have selected a statistical method in which according by subject, and, according to their DNA repair capacity level, the risk of development of breast cancer can be estimated in women. According to still further features in the described preferred embodiments of this invention, the risk of a woman developing breast cancer is expressed as a probability to eventually develop breast cancer according to her DNA repair capacity, age, gynecological history and other variables that have been found to be important predictors of breast cancer or potential confounders of the association between DNA repair capacity and breast cancer. The probability is calculated by using multiple logistic regression modeling based on a large case-control study in which newly diagnosed breast cancer women are compared to cancer-free women (controls). This control group had both a negative mammography and a normal clinical breast examination performed by a physician within six months of their DNA repair capacity measurement. According to still further features in the described preferred embodiments, the risk is expressed in probability of eventually developing breast cancer (lifetime risk) as related to the % DNA repair capacity of the woman being tested. Examples of the applicability of this method as a screening tool for women are provided in this invention.

DETAILED DESCRIPTION OF THE PREFERRED EMBODIMENTS OF THE INVENTION

Figure 1:
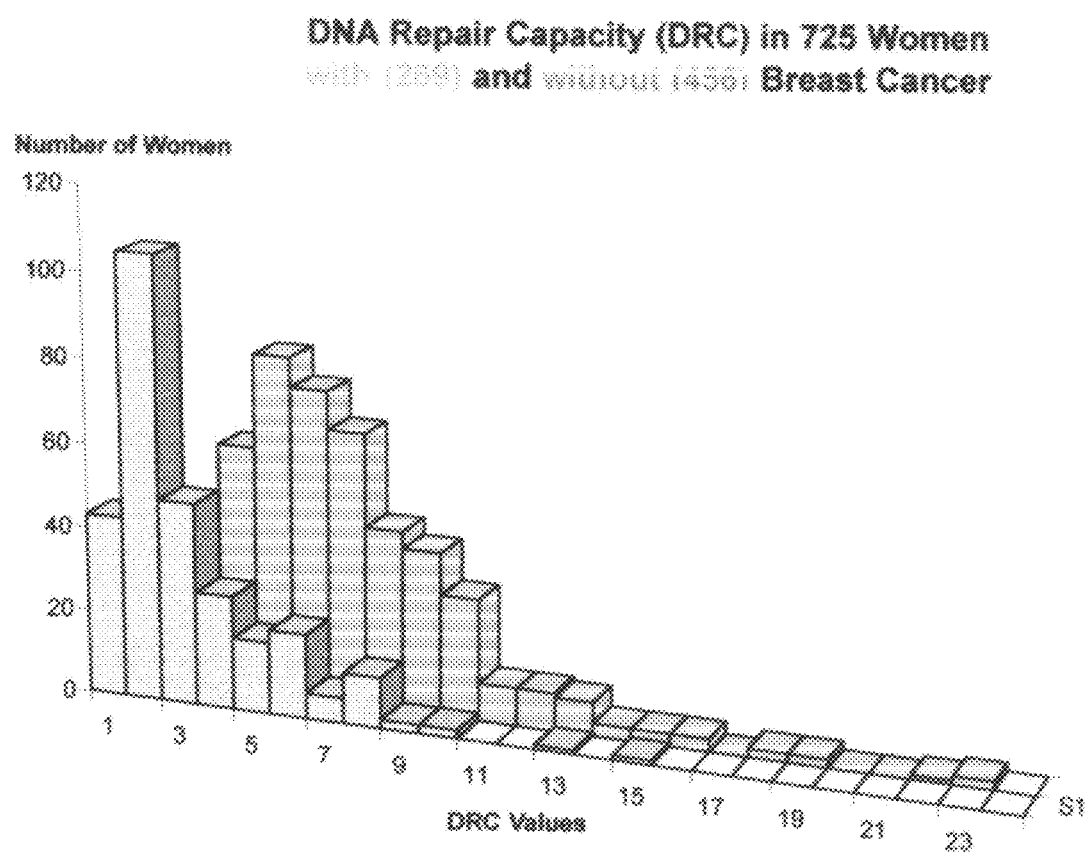
FIG. 1 shows the distribution of DNA repair capacity (DRC) in 725 women with (269) and without (456) breast cancer to illustrate the difference between them and thus the potential to use DRC to predict or diagnose breast cancer. Data from DRC breast cancer studies (Matta et al., 2009, unpublished data).

As part of the DNA repair capacity and breast cancer research project that was initiated in the laboratory of one of the inventors in 2002 and is still ongoing (2008), we analyzed the association and predictability of the DNA repair capacity (DRC) and breast cancer where we found a very strong association. The methods utilized to find that DRC can be utilized as a predictor of breast cancer are:

1. Blood Collection and Isolation of Lymphocytes from Women:

Thirty milliliters of peripheral blood is obtained from each woman (either a breast cancer patient or a control) who is collected in heparinized tubes. The lymphocytes are then isolated by the Ficoll gradient technique and suspended in freezing media containing 10% dimethyl sulfoxide, 40% RPMI-1640 medium, 50% fetal bovine serum and 1% antibiotic/antimycotic, and 2.0 ml aliquots stored in −80° C. freezer. These lymphocytes are later thawed in batches for the host cell reactivation assays (Qiao et al. 2002).

2. Measurement of the DNA Repair Capacity of Lymphocytes Using the Host-Cell Reactivation Assay:

The host reactivation assay that is described as part of the method in this invention has been used in several epidemiological studies of cancer (Wei et al. 1993, Cheng et al. 1998, Landi et al. 2002, Spitz et al. 2001, Matta et al. 2003, Ramos et al. 2004, Wei et al. 2003). A thorough discussion of the development and extensive validation of this assay with the luciferase reporter gene was published by Qiao et al. 2002. A summary of this assay has been described above. The assay is based in the fact that DNA can be transiently expressed (transfected) when introduced into a cell. If that DNA molecule is damaged, its expression will depend on the capacity of the host cell to repair that DNA damage. A non-replicating plasmid of 5 kilo bases was genetically engineered to contain a bacterial reporter gene that is not present in a mammalian cell. The gene is damaged by UV exposure in a controlled and quantitative manner (dose-response curve), and the level of its expression is a direct measure of the repair capacity of the host mammalian cell. This assay measures the total sum of the DNA repair capacity of lymphocytes, which is a reflection of the repair capacity of the donor and primarily measures DNA repair via the nucleotide excision repair pathway.

UV dosimetry of reporter gene plasmid—The peripheral blood lymphocytes previous frozen from each woman are assayed in batches as described by Ramos et al. 2004. The plasmid construct containing the luciferase gene is irradiated at 0, 350, and 700 $J/m^2$ using a 254 nm UVC lamp (Ramos et al. 2004). A detailed description of this plasmid construct has been published by Qiao et al. 2002. Peripheral blood lymphocytes with >95% viability are incubated for 72 hours with phytohemagglutinin and then are transfected with undamaged or damaged plasmid DNA. Cells isolated from xeroderma pigmentosum patients and corresponding to complimentary groups C and D (XPC, XPD) will be used as positive controls (Coriel Institute Medical Research cell lines GM 02246D and GM 02253F respectively). These cells provide and internal control for every determination of DNA repair capacity (DRC) because their DRC is well-known. After irradiation at 700 $J/m^2$, DRC is about 1-3% and 0-1% in XPC and XPD control cell lines.

Fetal cells (GM08925B, Coriel) are used to provide another internal positive control for normal DRC (approximately around 15%).

UVC radiation is utilized to damage the plasmid containing the reporter gene because results in samples from breast carcinoma patients are reproducible (Ramos et al. 2004). UVC completely damages the plasmid and produces all types of DNA damage. Because the host cell reactivation assay provides a measure of global DNA repair instead of specific pathways, the method utilized to damage the plasmid is not critical, provided that results are reproducible as presented in this invention.

3. Calculations of DNA Repair Capacity:

The standard assay for gene expression of luciferase activity is measured using a luminometer (Turner Designs, Model TD-20/20 or similar instrument). The percent DNA repair capacity (DRC) is then calculated based on luminescence counts as the percentage of residual luciferase gene expression (percentage luciferase activity) after repair of damaged plasmid DNA compared with undamaged plasmid DNA (100%). The measurement of DRC has a coefficient of variation of less than 10% both, in triplicate and repeated sample tests (Grossman and Wei 1994). With this precision, it has been demonstrated that this assay can distinguish the intra-assay variation (assay repeated on the same sample) and inter-assay variation (assay repeated on separate samples) by being able to maintain the ranks of samples measured in triplicate from multiple patients.

4. Statistical Methods for Using DNA Repair Capacity (DRC) to Predict Breast Cancer Risk:

Low DRC as a risk factor for breast cancer.—After analyzing DRC as a continuous (numerical) variable, DRC is divided in two levels (low and high) using the most efficient cut-off point (3.1%) in which we found DRC as a predictor of breast cancer with a 71.0% sensitivity and 90.2% specificity. The analysis is based on using the odds ratio (OR) as a measure of association: the ratio of the odds of BC between women with low DRC to those with high DRC. Using said method, we found that women with a low DRC level were 13.4 times more likely to have breast cancer than those with high DRC. After multivariate analysis using multiple logistic regression, in which the potential confounding effects of several variables simultaneously were adjusted (accounted for), this association increased to 21.4 times (table 1). In spite of the large variability (variance) found, the association of DRC and breast cancer was highly statistically significant ($p<0.000001$).

DRC to assess the lifetime risk of developing breast cancer.—Estimate the adjusted risk or probability of the woman being tested to eventually develop breast cancer using her DRC value on a multiple logistic regression equation we have calculated using available data from our database that now includes approximately 1,000 women encompassing about 350 breast cancer cases and 650 controls without breast cancer and adjusting for potential confounders as follows:

a) include the DRC percent obtained from the woman being tested as $X_1$ in the following multiple logistic regression equation:

$$P(Y=1)=\exp(b_0+b_1X_1+b_iX_i+\ldots+b_nX_n)/[1+\exp(b_0+b_1X_1+b_iX_i+\ldots+b_nX_n)]$$

where $P(Y=1)$ is the probability to eventually develop breast cancer, "exp" is the natural antilogarithm, $b_0$ is the constant, and each $b_i$ is the logistic regression partial coefficient for each of the n number of $X_i$ variables. In addition to the DRC value ($X_1$) for the woman being tested, the rest of the variables $X_i \ldots X_n$ in the logistic model are included because they either have an important contribution in the calculation of the probability of developing breast cancer $P(Y=1)$, or because they are potential confounders being adjusted for to obtain an estimate of the probability of eventually developing breast cancer after controlling for their confounding effect in the relationship between DRC and breast cancer; and b) Calculate the probability of developing cancer with the previous multiple logistic regression by using a statistical software such as SAS, SPSS, or Stata.

Figure 2:
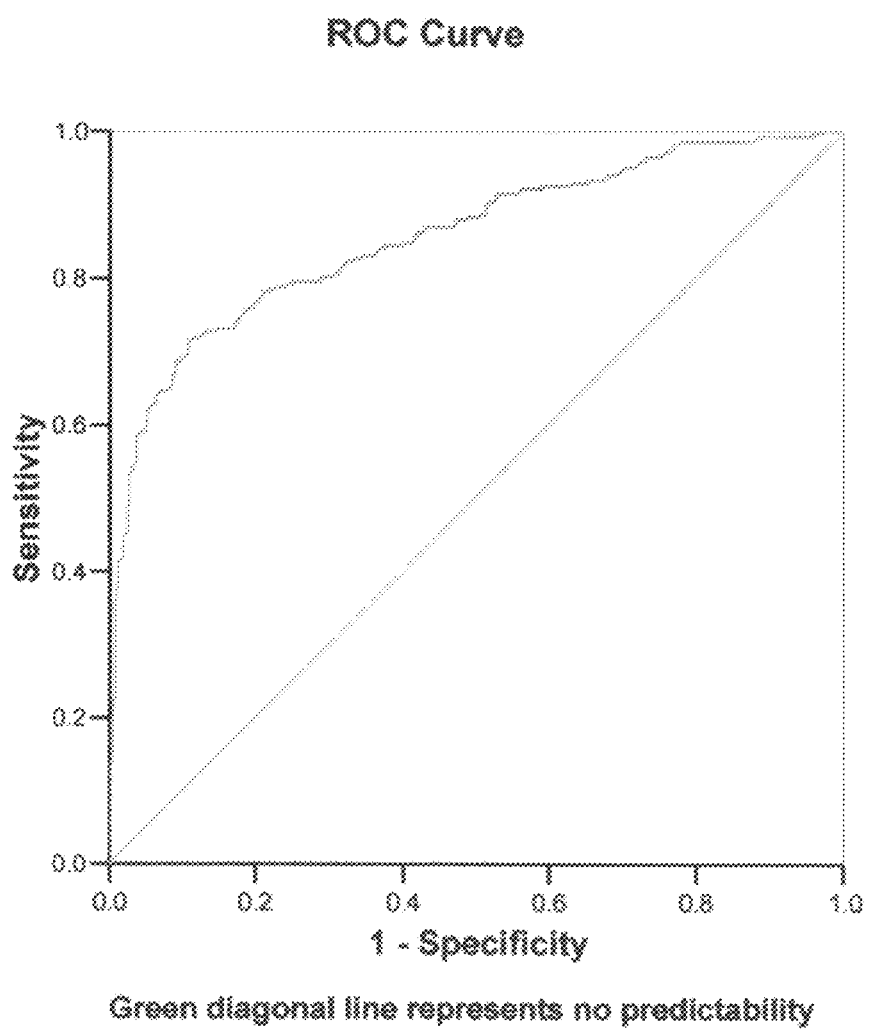
FIG. 2 shows a Receiver Operating Characteristic (ROC) curve analysis (Metz 1978, Zweig and Campbell 1993) assessing the breast cancer predictability or the diagnostic potential of DRC (Griner et al., 1981). The ROC curve showed 83.9% area under the curve indicating a large predictability of breast cancer as compared to the diagonal line depicting 50.0% area of no predictability (the area under the curve indicates how predictable the test is from 50-100%). Results based on data from 725 women (cases and controls), the same study group presented in FIG. 1.

DRC as a screening test to predict breast cancer.—In this invention, we have also evaluated DRC as a predictor of BC, using the cut-off point of 3.1% (95% Confidence Intervals (CI): 2.9% to 3.3%) of DRC when the sensitivity was 71.0% (95% CI: 66.4% to 77.2%), and the specificity reached 90.2% (95% CI 86.5% to 93.9%). Low DRC was a value as low or lower than 3.1% (positive test), and high DRC value whenever DRC value was higher than 3.1% (negative test). The receiver operating characteristic (ROC) curve analysis (Metz 1978, Zweig and Campbell 1993) was used to assess the diagnostic potential of DRC (Griner et al., 1981). ROC analysis showed a large predictability of breast cancer (85.9%) that was highly statistically significant ($p<0.0001$) as compared to 50.0% or no predictability (Table 2, and FIG. 2 show the ROC curve of DNA repair capacity as a predictor of breast cancer). The predictive values of the 3.1% level of DRC were calculated as they measure the probability to detect breast cancer when a woman being tested has high or low DRC level. If the woman has a low DRC level (positive test), the predictive value or probability to have BC ranged from 0.7% to 98.5% as related to the BC prevalence level of the population from where the woman comes from, being 0.1 to 90 per 100 respectively. Whenever a woman has high level of DRC (negative test) the predictive values to rule out BC ranged from 25.7% to 100% for the same range of BC prevalence (Table 3). These results show that this level of DRC (3.1%) has a strong potential value as a biomarker, being very useful to rule out disease in low prevalence or low risk populations, and useful to confirm it in high prevalence or high risk populations. Therefore, when DNA repair capacity is utilized as described in this invention, it can be used as a screening test for breast carcinoma especially in populations with low prevalence of breast cancer that is usually the case during screening programs.

TABLE 1

Crude and adjusted association of the DNA repair capacity (DRC) and breast cancer (BC) measured with the crude[1] and the adjusted[2] Odds Ratio[3], their 95% confidence intervals (95% CI), and statistical significance (p-value).

| | Variable | | | | |
|---|---|---|---|---|---|
| DRC | BC Cases | BC-Free Controls | Crude Odds Ratio (95% CI) | Adjusted Odds Ratio (95% CI) | p-value |
| Low[4] | 191 | 46 | 21.8 (14.6, 32.7) | 32.4 (20.2, 52.0) | <0.0001 |
| High[4] | 78 | 410 | | | |

[1]Crude or unadjusted analysis: the analysis is carried out without taking into consideration potential confounders
[2]Adjusted analysis: the analysis is carried out adjusting for the potential effect of all confounding variables simultaneously by using regression techniques (multiple logistic regression). The odds ratio was adjusted by age, body mass index, family history of breast cancer, number of children, marital status, ever breastfeed, irregular menstrual periods, alcohol use, and smoking.
[3]Odds ratio (OR) is the ratio of the odds of BC between women with low DRC to those with high DRC.
[4]Low DRC is ≤3.1%, high DRC is >3.1%

TABLE 2

Test results of DRC as a predictor of breast cancer in 725 women: predictability or area under the ROC Curve[1]

| Predictability or area under the curve | Standard Error[a] | Asymptotic Statistical significance or p-value[b] | Asymptotic 95% confidence interval for the predictability or area under the curve | |
|---|---|---|---|---|
| | | | Upper Bound | Lower Bound |
| 85.9% | 1.5% | <0.0001 | 82.9% | 88.9% |

[1]The receiver operating characteristic (ROC) curve analysis (Metz 1978, Zweig and Campbell 1993) was used to assess the diagnostic potential of DRC (Griner et al., 1981). ROC analysis showed a large predictability of breast cancer that was highly statistically significant as compared to 50.0% or no predictability (85.9% of the area under the curve indicates how predictable the test is from 50-100%)
[a]Under the nonparametric assumption
[b]Null hypothesis: true area = 50%

TABLE 3

DRC Predictability: predictive values for Breast Cancer (BC) using 3.1% DNA Repair Capacity level or lower; 71.0% sensitivity and 90.2% specificity for women from populations with BC prevalence between 0.1 to 90 per 100.

| Prevalence of BC per 100 | Probability to have BC whenever DRC is 3.1% or lower (% Positive Predictive Value) | Probability of not having BC whenever DRC is higher than 3.1% (% Negative Predictive Value) |
|---|---|---|
| 0.1 or lower | 0.7 | 100.0 |
| 0.2 | 1.4 | 99.9 |
| 0.3 | 2.1 | 99.9 |
| 0.4 | 2.8 | 99.9 |
| 0.5 | 3.5 | 99.8 |
| 01 | 6.8 | 99.7 |
| 02 | 12.9 | 99.4 |
| 03 | 18.3 | 99.0 |
| 04 | 23.2 | 98.7 |
| 05 | 27.6 | 98.3 |
| 10 | 44.6 | 96.6 |
| 20 | 64.4 | 92.6 |
| 30 | 75.6 | 87.9 |
| 50 | 87.9 | 75.7 |
| 70 | 94.4 | 57.1 |
| 90 | 98.5 | 25.7 |

As an example of the potential application of this methodology as a biomarker for breast cancer, we present in this invention, the utility of said method on predicting a type of breast cancer; infiltrating ductal breast carcinoma (IDBC). This is the most common type of breast cancer, and we only included married women as we found that this population seeks medical attention more regularly than the rest of the women and thus provide more reliable health information. Using the same DRC cut-off point of 3.1%, the unadjusted odds ratio found was 63.2 and after multivariate analysis, this association increased to 89.0. Therefore, married women that have low a DRC level as defined in this invention are 89 times more likely to have IDBC. In spite of the small sample size, these associations were highly statistically significant ($p<0.0001$).

We also evaluated DRC as a predictor of the infiltrating ductal breast carcinoma (IDBC) in married women using the said cut-off point of 3.1% of DRC reaching a sensitivity of 87.7% and specificity of 89.3%. The ROC curve analysis showed a very large predictability potential for IDBC (96.0%) that was highly statistically significant ($p<0.0001$) as compared to 50.0% or no predictability. The predictive values of the said level of DRC were calculated to measure the probability to detect IDBC when a married woman being tested has high or low DRC level. If the married woman had a low DRC level, the predictive value or probability to have IDBC ranged from 0.8% to 98.7% as related to the IDBC prevalence level of the population from where the woman comes from, being 1 to 90 per 100 respectively. Whenever a married woman had high level of DRC, the predictive values to rule out IDBC ranged from 44.7% to 100% for the same range of IDBC prevalence. The results of this example show that this level of DRC (3.1%) has a high potential value as a biomarker, being very useful to rule out disease. Therefore, as demonstrated in this example, when DNA repair capacity is utilized as described in this invention, it can be used as a powerful screening test for infiltrating ductal breast carcinoma especially in populations with low prevalence of this disease that is usually the case during screening programs.

The invention claimed is:

1. A method for using DNA repair capacity (DRC) as a blood biomarker to calculate the risk of a female subject developing breast cancer, comprising:
   a) obtaining lymphocytes isolated from the subject wherein the lymphocytes comprise non-replicated expression plasmids comprising a luciferase reporter gene that has been exposed to ultraviolet radiation C (UVC);
   b) calculating a percent DRC for the subject as the percentage of residual luciferase gene expression after repair of damaged plasmid DNA as compared to luciferase gene in cells comprising non-replicating expression plasmids comprising a luciferase reporter gene that has not been exposed to UVC; and
   c) classifying a subject with a percent DRC below 3.1% as being at risk for breast cancer and classifying a subject with a percent DRC above 3.1% as being at low risk for breast cancer.

2. The method of claim 1, further comprising estimating an adjusted risk of the subject to develop breast cancer using the following equation:

$$P(Y=1) = \exp(b_0 + b_1 X_1 + b_i X_i + \ldots + b_n X_n)/[1 + \exp(b_0 + b_1 X_1 + b_i X_i + \ldots + b_n X_n)]$$

wherein $P(Y=1)$ is a probability to eventually develop breast cancer, "exp" is the natural antilogarithm, $b_0$ is a constant, and each $b_i$ is the logistic regression partial coefficient for each of the n number of $X_i$ variables.

* * * * *